United States Patent [19]

Chen et al.

[11] Patent Number: 5,380,790
[45] Date of Patent: Jan. 10, 1995

[54] PROCESS FOR THE PREPARATION OF ACRYLIC POLYMERS FOR PHARMACEUTICAL COATINGS

[75] Inventors: Robert G. Chen; Stephen H. Wu, both of Kingsport, Tenn.

[73] Assignee: Eastman Chemical Company, Kingsport, Tenn.

[21] Appl. No.: 118,903

[22] Filed: Sep. 9, 1993

[51] Int. Cl.$^6$ .................. C08K 5/41; C08L 33/00; A61K 9/32
[52] U.S. Cl. ..................... 524/745; 524/723; 524/767; 524/833; 424/482
[58] Field of Search ............... 524/539, 560, 745, 767, 524/833, 379, 723; 526/181, 234, 318.4; 424/482

[56] References Cited

U.S. PATENT DOCUMENTS

| | | | |
|---|---|---|---|
| 3,035,004 | 5/1962 | Glavis | 524/833 |
| 4,017,647 | 4/1977 | Ohno et al. | 427/3 |
| 4,081,418 | 3/1978 | Barua et al. | 260/29.6 |
| 4,112,215 | 9/1978 | Boensler et al. | 528/503 |
| 4,138,380 | 2/1979 | Barabas et al. | 524/833 |
| 4,177,177 | 12/1979 | Vanderhoff et al. | 260/29.2 M |
| 4,330,338 | 5/1982 | Banker | 106/197 C |
| 4,462,839 | 7/1984 | McGinley et al. | 106/198 |
| 4,518,433 | 5/1985 | McGinley et al. | 106/180 |
| 4,775,536 | 10/1988 | Patell | 424/471 |
| 5,025,004 | 6/1991 | Wu et al. | 514/165 |
| 5,047,258 | 9/1991 | Belanger et al. | 427/3 |
| 5,118,749 | 6/1992 | Knutson | 524/560 |
| 5,182,327 | 1/1993 | Biale | 524/560 |

FOREIGN PATENT DOCUMENTS 2057876  4/1991  United Kingdom .

OTHER PUBLICATIONS

Lehmann and Dreher, Pharm. Ind., vol. 34, No. 11a, pp. 894–899 (1972).
N. Sütterlin, Makronol. Chem., Suppl. 10/11, 403–418 (1985).
K. Lehmann, APV-Informationdienst, vol. 18, No. 1, 48–60 (1972).
H. Kast, Makromol. Chem., Suppl. 10/11, 447–461 (1985).
E. S. Daniels & A. Klein, Progress in Organic Coatings, 19, 359–378 (1991).
K. Lehmann, Acta Pharmaceutica Technologica, 31 (2), (1985).
J. P. Dechesne et al, J. Pharm, Belg., vol. 37, No. 4, pp. 273–282, (1982).
J. Colloid Science, 6, 108 (1951).
J. A. Seitz, "Encyclopedia of Pharmaceutical Technology", vol. 1, Edited by J. Swarbrick and J. Boylan, 337 (1988).
G. S. Banker and G. E. Peck, Pharmaceutical Technology, 5 (4), 55–61 (1981).
R. E. Pondell, Drug Development and Industrial Pharmacy, 10 (2), 191–202 (1984).
M. B. Davis, G. E. Peck and G. S. Banker, Drug Development and Industrial Pharmacy, 12 (10), 1419–1448, (1986).
F. Gumowski, E. Doelker, and R. Gurny, Pharmaceutical Technology, 11 (2), 26–32, (1987).
R. K. Chang, C. H. Hsiao, and J. R. Robinson, Pharmaceutical Technology, 11 (3), 56–68, (1987).
J. Gardon, High Polymers, vol. 29, Wiley, New York, 143 (1977).
U.S.P. XXII/NF XVII, U.S. Pharmacoplial Convention, Inc., 1990, as USP Methacrylic Acid Copolymer—Type C.

*Primary Examiner*—Tae H. Yoon
*Attorney, Agent, or Firm*—Bernard J. Graves, Jr.

[57] ABSTRACT

Provided is a process useful for preparing acrylic polymers of methacrylic acid and ethyl acrylate. The process provides polymers useful as enteric coatings for medicaments in solid form, said coatings having improved effectiveness, reproducibility and coating efficiency. Also provided are medicaments in solid form coated with such polymers.

7 Claims, 3 Drawing Sheets

SCHEMATICS OF LATEX FILM FORMATION MECHANISMS

PROCESS FOR THE PREPARATION OF ACRYLIC POLYMERS FOR PHARMACEUTICAL COATINGS

FIELD OF THE INVENTION

This invention relates to a process for making polymers of methacrylic acid and ethyl acrylate having improved effectiveness, reproducibility, and coating efficiency, which are useful as pharmaceutical coatings for dosage forms such as tablets.

BACKGROUND OF THE INVENTION

Acrylic latexes of methyl methacrylate, ethyl acrylate, and methacrylic acid have been used in milkcan linings and paper coatings in the food-packaging industry since about 1950, and such dispersions were specified in the U.S. Federal Register for food additives in 1961. Copolymers of ethylacrylate and methacrylic acid for enteric coatings were developed by Lehmann and Dreker in "Anwendung wässriger Kunststoff-dispersioner zum überzieken von Arzneiformen," Pharm. Ind., 34, 894–899 (1972).

Ethyl acrylate-methacrylic acid latexes can be prepared by emulsion polymerization. The emulsion polymerization mechanism of acrylate monomers with hydrophilic methacrylic acid comonomer is described by N. Sütterlin in "Structure/Property of Emulsion Polymers," Makromol. Chem. Suppl. 10/11, 403–418 (1985). For pharmaceutically useful polymethacrylates, the polymerization mechanism is described by K. Lehmann in "herstellung von Acrylharz-Filmtabletten mit gesteuerter Winkstoffabgabe nach verschiedenen Sprühverfahren," APV-Informationdienst 18 (1), 48–60 (1972).

Methacrylic acid-ethyl acrylate copolymer for enteric coatings is defined in U.S.P. XXII/NF XVII, U.S. Pharmacopeial Convention, Inc., 1990, as USP Methacrylic Acid Copolymer—Type C.

A 30% aqueous dispersion of the copolymer of ethyl acrylate and methacrylic acid is commercially available from Röhm GmbH, Darmstadt, Germany, under the tradename EUDRAGIT® L30D. Chemistry and application properties are described by K. Lehmann in *Aqueous Polymeric Coatings for Pharmaceutical Dosage Form*, J. W. McGinity ed., Marcel Dekker, 1989, pp. 153–245.

EUDRAGIT® L30D is manufactured by emulsion polymerization of about 1:1 mole-ratio of methacrylic acid and ethyl acrylate; sodium lauryl sulfate and polysorbate 80 are used as the emulsifiers. The initiators are generally peroxygen compounds, which are chemically bonded to the polymers and are normally not found in substantial amounts in the final latex. The residual monomers can be either reduced or even eliminated by optimizing the polymerization process or by final steam distillation. Total residual monomer content in commercial EUDRAGIT® products is below 0.3%; normally less than 0.1% is found.

In the preparation of methacrylic acid-ethyl acrylate emulsion polymers for enteric coatings, food grade sodium lauryl sulfate is commonly used as primary emulsifier in combination with the food grade, nonionic surfactant polysorbate 80 as co-emulsifier. Although these emulsifiers are quite effective in preparing emulsion polymers, tablets coated with such emulsion polymers may be more sensitive to aqueous solution, including gastric fluid—this phenomenon may be attributed to the hydrophilic characteristics of sodium lauryl sulfate. Thus, the effectiveness in gastric fluid may be reduced.

The effectiveness of a methacrylic acid-ethyl acrylate enteric polymer for coating of tablets generally depends on the rate of film forming during the coating of the tablet and the development of the cohesives film strength. When a methacrylic acid-ethyl acrylate emulsion polymer is used for enteric coating of pharmaceutical dosage forms, the polymer particles are deposited from an aqueous dispersion of discrete polymer spheres. Individual submicrometer-size spheres, each containing hundreds of polymer chains, coalesce into a continuous film as the water evaporates.

Kast describes the film formation mechanism for linear, non-crosslinking polymer particles in *Makromol. Chem. Suppl.* 10/11, 447 (1985). The film formation mechanism can be divided into three phases:

a) evaporation of water or drying;
b) coalescence and deformation of latex particles; and
c) cohesive strength development by the further gradual coalescence of adjacent latex particles and the interdiffusion of polymer chains from adjacent particles.

A conceptual visualization is depicted by Daniels et al., in *Progress in Organic Coatings*, 19, pp. 359–378 (1991). Three mechanisms which result in the development of cohesive strength in polymer films from latices are shown in FIG. 1 therein. The resulting latex dispersion consists of spheres that are suspended and separated by electrostatic repulsion. As water evaporates, interfacial tension between water and polymer pushes particles into point contact in a close-packed ordered array. A strong driving force is necessary to overcome repulsive forces, deform the particles, and cause the spheres to fuse, thereby resulting in complete coalescence. Capillarity caused by the high interfacial surface tension of water provides the driving force to fuse the particles, and plasticizer inclusion in the dispersion swells and softens the polymer spheres, thereby facilitating coalescence and reducing minimum film-formation temperatures.

The polymer spheres are pulled closer together as a result of surface tension (water-air interfacial tension) or capillarity as the surrounding water film constricts. Energy required for the coalescence of spheres results from the surface tension of the polymer generated by the negative curvature of the particle surface and according to Dillon et al., in *J. Colloid Science*, 6, 108 (1951) may be described by Frenkel's equation as follows:

$$\theta^2 = \frac{3\gamma t}{2\pi r} \eta$$

where $\Theta$ is one-half the angle of coalescence (contact angle) at time t; $\gamma$ is the surface or interfacial tension, r is the radius of a sphere and $\eta$ is the viscosity of the spheres.

This equation illustrates the inverse relationship between internal viscosity ($\eta$) of the spheres and the driving force ($\gamma$) necessary to fuse or coalesce discrete particles. Further, it is evident that smaller-radius polymer spheres require less driving force (capillarity) to completely fuse or coalesce.

On the microscopic or molecular level, once the polymer particles are in contact with one another, molecular interdiffusion of macromolecules from one particle into its neighbor occurs, and their entanglement takes place. The formation of entanglements between polymer chains of adjacent particles is crucial to the development of mechanical strength of the resulting films. Generally, higher molecular weight polymer chains develop better entanglement and, as a result, cohesive strength.

Thus an effective methacrylic acid-ethyl acrylate enteric polymer should ideally have smaller particle size and adequate lower molecular weight polymer chains for rate of film forming, and also have a small portion of slightly higher molecular weight polymer chains for developing cohesive film strength.

The use of EUDRAGIT® L30D for the enteric coating of tablets has been described by Lehmann in *Acta Pharmaceutica Technologica,* 31, 96–106 (1988); Dechesne et al. in J. Pharm. Belg. 37, 273–282 (1982); Belanger et al. in U.S. Pat. No. 5,047,258 (1991) and Patell et al. in U.S. Pat. No. 4,775,536 (1988).

Although there are many publications describing the use of EUDRAGIT® L30D for the enteric coating of pharmaceutical dosage forms, it is generally believed that the amount of the acrylic dispersion required for enteric coating is still high. It would therefore be desirable to develop an improved composition and process for making such useful methacrylic acid-ethyl acrylate copolymers which will provide an effective coating at lower coating weight.

In addition, because of the slower evaporation rate of water as compared to solvent, the coating time for waterborne acrylic coatings is generally longer than that for solvent-borne enteric coatings. It would therefore be desirable to develop an improved composition and process for making such methacrylic acid-ethyl acrylate copolymers which may have improved coating efficiency. The amount and the time required for coating would thus be reduced.

Further, it is generally perceived that the consistency during the coating process and thereby the coating performance of a waterborne acrylate enteric coating on tablets is not fully satisfied. It would thus be desirable to develop an improved polymeric composition which will reduce the batch to batch variation.

Film coatings are applied to pharmaceutical dosage forms to 1) facilitate the swallowing of the dosage form, 2) control the release of the drug, either protecting the drug from the gastric environment of the stomach or reducing potential gastric irritation caused by high localized drug concentration, 3) protect the drug from the storage environment, 4) improve the appearance, and 5) mask undesirable tastes, odors and colors. Coatings are commonly applied from organic solutions of various polymers such as cellulose acetate phthalate (CAP) and hydroxypropyl methylcellulose phthalate (HPMCP). Because of environmental concerns and the increase in cost of suitable solvents, it is desirable to apply coating compositions via an aqueous medium.

An enteric coating is defined in USP XXII as a coating which is intended to delay the release of the medication until the dosage form has passed through the stomach. Enteric coated tablets are thus one form of delayed release dosage forms.

The following references provide general background information on enteric coating methodology:

*Drugs and the Pharmaceutical Sciences,* vol. 36: "Aqueous Polymeric Coatings for Pharmaceutical Dosage Forms", edited by J M McGinity, Marcel Dekker Inc, New York, N.Y., 1989.

*Handbook of Pharmaceutical Excipients,* Published by American Pharmaceutical Association, Washington, D.C., 214 (1986).

J. A. Seitz, "Aqueous Film Coating", *Encyclopedia of Pharmaceutical Technology,* vol. 1, edited by J. Swarbrick and J. Boylan, 337 (1988).

G. S. Banker and G. E. Peck, "The New, Water-Based Colloidal Dispersions," *Pharmaceutical Technology,* 5(4), 55–61 (1981).

R. E. Pondell, "From Solvent to Aqueous Coatings," *Drug Development and Industrial Pharmacy,* 10(2), 191–202 (1984).

M. B. Davis, G. E. Peck, and G. S. Banker, "Preparation and Stability of Aqueous-Based Enteric Polymer Dispersions," *Drug Development and Industrial Pharmacy,* 12(10), 1419–1448 (1986).

F. Gumowski, E. Doelker, and R. Gurny, "The Use of a New Redispersible Aqueous Enteric Coating Material," 11 (2), 26–32 (1987).

R. K. Chang, C. H. Hsiao, and J. R. Robinson, "A Review of Aqueous Coating Techniques and Preliminary Data on Release from a Theophylline Product," 11(3), 56–68 (1987).

The common methods of eliminating or minimizing organic solvents in a coating process for preparing pharmaceutical dosage forms include the following:

1. A coating system which employs a solution of coating polymer in a mixed organic and aqueous solvent system such as hydroxypropyl methylcellulose (HPMC) in ethanol/water. This method only partially eliminates the need for organic solvents.

2. A coating system which employs an aqueous solution of water-soluble film-forming polymer. This method is limited to water-soluble polymers such as methylcellulose (MC), hydroxypropyl cellulose (HPC), and HPMC. Another limitation is the need to remove a large amount of water during drying and coating processes.

3. A coating system which employs an aqueous solution of alkali salt of an enteric polymer such as sodium or ammonium salt of hydroxypropyl methylcellulose phthalate (HPMCP), polyvinylacetate phthalate (PVAP), or cellulose acetate phthalate (CAP).

U.S. Pat. No. 4,017,647 teaches a method for providing enteric coatings on solid pharmaceutical dosage forms in which enteric coatings are provided on solid dosage forms by coating the dosage forms with an aqueous solution of a polymeric substance having carboxyl groups in a water-soluble salt form and bringing thus coated dosage forms into contact with an inorganic acid to convert the polymeric substance into the acid form, which is insoluble in water.

U.K. Patent Application GB No. 2,057,876 teaches a method of preparing coated medicament-containing cores of a solid unit dosage form with an enteric coating. The coating was applied (e.g., in a coating pan) onto the medicament cores from an aqueous solution of a water soluble salt of a cellulose partial ester of a dicarboxylic acid, the aqueous solution being free from organic solvent, until an enteric coating around each medicament core had been built up. The salt may be a sodium or ammonium salt of HPMCP or CAP.

4. A coating system which employs the pseudolatex of a water-insoluble film-forming polymer. Pseudolatex is an aqueous colloidal dispersion of polymer which is, for practical purposes, indistinguishable from a true latex. However, it is prepared by employing a mechanical method of converting a pre-existing water-insoluble polymer into an aqueous colloidal dispersion.

U.S. Pat. No. 4,177,177 teaches a polymer emulsification process comprising intimately dispersing a liquified water insoluble polymer phase at a certain viscosity in an aqueous liquid medium phase (at a certain ratio and temperature) containing at least one nonionic, anionic, or cationic oil-in-water emulsifying agent at a certain concentration in the presence of an emulsion stabilizer at a certain concentration selected from the group consisting of those hydrocarbons and hydrocarbyl alcohols, ethers, alcohol esters, amines, halides, and carboxylic acid esters which are inert, nonvolatile, water insoluble, liquid, and contain a terminal aliphatic hydrocarbyl group of at least about 8 carbon atoms and mixtures thereof, and subjecting the resulting crude emulsion to the action of comminuting forces sufficient to enable the production of an aqueous emulsion containing polymer particles averaging less than 0.5 micron in size. This patent teaches that the disclosed polymer emulsification process is carried out at a temperature of about 40° to 90° C.

U.S. Pat. No. 4,330,338 teaches a coating composition for pharmaceutical dosages. The dosages use a set of FDA-approved polymers with a long history of pharmaceutical and food use. Pseudolatices containing such polymers are used to produce soluble, enteric, or sustained release coatings when the formulations are applied to dosage forms.

U.S. Pat. No. 4,462,839 teaches a process for making a polymeric powder which is readily dispersible in water to provide a composition useful for forming an enteric coating on pharmaceutical dosage forms, comprising of providing a freshly prepared spherical water-insoluble enteric polymer particles, adding to said dispersion a phosphate salt in an amount sufficient to minimize coalescence of particles during spray drying. U.S. Pat. No. 4,518,433 teaches a similar process except acetylated monoglyceride is added to the dispersion before spray drying to produce the water-redispersible powder.

U.S. Pat. No. 5,025,004 discloses a process for preparing polymeric compositions which are suitable for coating medicaments or for use in cosmetic formulations and the novel compositions prepared therefrom. The process makes stable, colloidal, latex-like dispersions of coating polymers which can be readily dried to form polymeric powder materials. The process makes use of a novel combination of a water-in--oil emulsifier and an oil-in-water emulsifier.

5. A coating system which employs a true latex of film-forming polymer prepared by emulsion polymerization of acrylic or methacrylic monomers.

Emulsion polymerization is a complex empirical art and usually involves more than four ingredients and often more variations in reaction conditions. (See, for example, J. Gardon in "Emulsion Polymerization," in *High Polym.*, Vol. 29, Wiley, N.Y. 143 (1977):

"This latex technology has become a complex empirical art. Subtle modifications in the composition of the recipes or in the method of synthesis can cause commercially significant changes in the end products obtained from vinyl-type or ethylenic monomers.")

Copolymers having a wide range of complicated structures for varying applications may be prepared through process design and choice of ingredients such a monomers, initiators, emulsifiers and chain transfer agents in an emulsion polymerization. The final properties are greatly influenced by the choice of emulsifiers, the choice of initiators, the choice of other ingredients, the reaction temperature, and the method of monomer addition.

SUMMARY OF THE INVENTION

Figure 1:
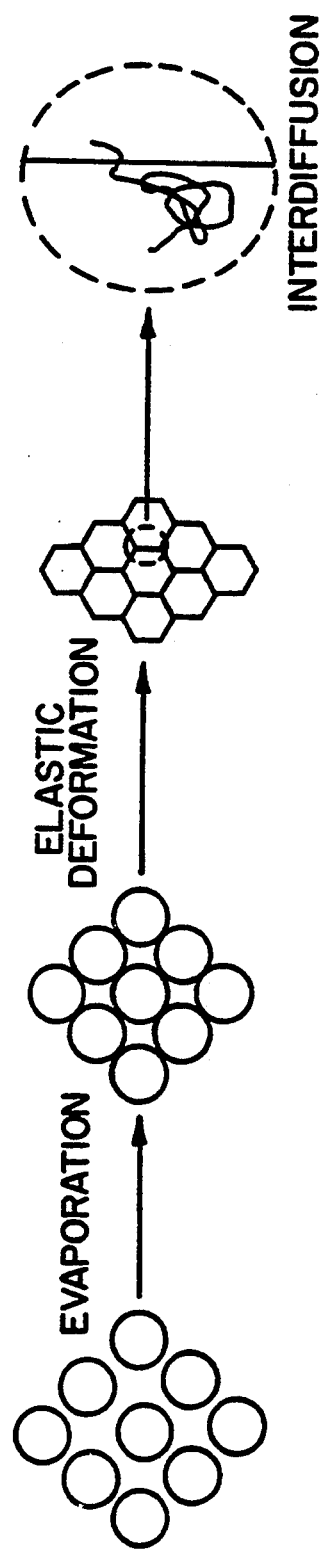
FIG. 1 is a schematic representation of the latex film formation mechanism.

The acrylate polymers of methacrylic acid and ethyl acrylate of the present invention are prepared by a semi-continuous emulsion polymerization process using 0.4 to 1.5% of sodium docusate and 0 to 4.0% of polysorbate as emulsifiers. Weight average molecular weights of the described acrylate enteric polymers are between 140,000 to 280,000, and have a polydispersity value of 2.5 to 10.0 ($M_W/M_N$). The described acrylate enteric polymers are monodispersed with a mean particle size less than 0.15 microns and a standard deviation less than 0.045. The polymer composition is stable and insoluble in the acidic aqueous medium with a pH value ranging from 1.0 to about 5.0 but soluble in aqueous medium with a pH greater than about 5.5.

The enteric polymers of the present invention have improved effectiveness, reproducibility, and reduced coating cycle for enteric coating of tablets over the commercially-available USP methacrylic copolymer-Type C enteric polymer, e.g., EUDRAGIT ® L30D. The described acrylate enteric polymers are prepared by a semi-continuous emulsion polymerization, comprising: 1) 0.4 to 1.5% of sodium docusate, 2) 0 to 4.0% of polysorbate, 3) 10 to 20% of ethyl acrylate, 4) 10 to 20% of methacrylic acid, 5) 0 to 1.0% of isopropyl alcohol (USP), 6) 0 to 0.2% of monothioglycerol NF or cysteine hydrochloride USP, 7) 60 to 75% of distilled or deionized water, and 8) a redox initiator selected from peroxygen compounds such as potassium persulfate and a reducing agent such as iron II sulfate hepta hydrate.

The described polymer is particularly useful as an enteric coating which protects the dosage forms containing an active ingredient in the gastric environment but releases the drug in the small intestines. In this regard, the only limitation on such active ingredient is that it should be one that is intended to be absorbed in the small intestine.

DETAILED DESCRIPTION OF THE INVENTION

The present invention provides a process for preparing a polymer of acrylate enteric polymers of methacrylic acid and ethyl acrylate comprising reacting (a) about 0.4 to 1.5 weight percent of sodium docusate;

(b) about 0 to 4.0 weight percent of polysorbate 80;

(c) about 10 to 20 weight percent of ethyl acrylate;

(d) about 10 to 20 weight percent of methacrylic acid;

(e) about 0 to 1.0 weight percent of isopropyl alcohol;

(f) about 0 to 0.2 weight percent of monothioglycerol or cysteine hydrochloride;

(g) about 60 to 75 weight percent of distilled or deionized water; and (h) about 0.02 to 0.15 weight percent of an initiator selected from the group consisting of sodium persulfate, potassium persulfate, ammonium persulfate, hydrogen peroxide, lauryl peroxide, benzoyl peroxide and optionally a compound selected from the group consisting of sodium bisulfite, sodium metabisulfite, sodium dithionate, sodium formaldehyde sulfoxylate, ascorbic acid and salts of $Fe^{+2}$;

at a temperature of about 30° C. to 85° C.

The choice of emulsifier is probably the most important factor in designing an emulsion polymerization. In this invention, a much less hydrophilic, food grade emulsifier, sodium docusate, (supplied by American Cyanamid Co. as COMPLEMIX® 100) is preferably used as the primary emulsifier in the ranges between 0.4 to 3%; and preferably between 0.6 to 1.5%. A food grade, non-ionic emulsifier polysorbate 80 is preferably used as the secondary emulsifier in the ranges between 0 to 4%; preferably 0.2 to 1.5%.

Initiators used in this invention are peroxygen compounds such as persulfates of sodium, potassium or ammonium, hydrogen peroxide, t-butylhydroperoxide, cumene hydroperoxide, lauryl peroxide, benzoyl peroxide, and persulfate compounds are preferred at a concentration between 0.02 to 0.15% in the emulsion. Redox initiators such as combination of peroxygen compounds with sodium bisulfite, sodium metabisulfite, sodium dithionate, sodium formaldehyde sulfoxylate, ascorbic acid and divalent iron salts; the total concentrations of the peroxygen compound/reductant/metallic compound are preferably between 0.02 to 0.15% in the emulsion.

Reaction temperature is generally related to the type and concentration of emulsifiers and initiators used in the emulsion polymerization. Reaction temperatures in this invention are in the range of about 30° C. to 85° C.; preferably between 60° and 85° C.

In this process, the concentration of sodium docusate is preferably about 0.6 to 1.5%; polysorbate 80 is present in a concentration of about 0.2 to 1.5%; isopropyl alcohol is present in a concentration of about 0.1 to about 0.8%; and the monothio-glycerol or cysteine hydrochloride is present in a concentration of about 0.03 to about 0.15%.

Methacrylic acid-ethyl acrylate enteric polymers are pH sensitive polymers, i.e. their solubility increases with pH value through neutralization of carboxylic acid functional groups. The range of compositions prepared from methacrylic acid and ethyl acrylate can be varied quite widely, but an approximate 1:1 ratio has been found to be a highly effective enteric coating for pharmaceutical products.

As noted above, a more effective methacrylic acid-ethyl acrylate enteric polymer should have smaller particle size and adequate lower molecular weight chains for rate of film forming, and also have a small portion of slightly higher molecular weight polymer chains for developing cohesive film strength. Thus, development of a process for making methacrylic acid-ethyl acrylate enteric polymer with smaller particle size and certain range of molecular weight distribution is desired. More specifically, mean particle size ranges from 0.07 to 0.15 microns, and 0.09 to 0.13 microns is preferred. Standard deviation of particle size distribution ranges from 0.015 to 0.045, and 0.019 to 0.035, i.e. mono-disperse particle size is preferred. Weight average molecular weight ranges from 140,000 to 280,000; and 160,000 to 250,000 is preferred. Polydispersity of a regular free-radical initiated emulsion polymer is about 2 to 4; however, the methacrylic acid-ethyl acrylate enteric polymers of the present invention exhibit a polydispersity of 2.5 to 10.0, and the preferred range is 3 to 6.

Mercaptans such as dodecyl mercaptan, t-butyl mercaptan, and halogenated compounds such as carbon tetrabromide and bromodichloromethane can be used to regulate the molecular weight of emulsion polymers for industrial applications. These compounds, however, are rather toxic and thus not generally suitable for pharmaceutical applications. We have found that in our process, isopropyl alcohol, monothioglycerol NF, and cysteine hydrochloride-USP can be successfully used to regulate molecular weight of acrylic latexes for pharmaceutical applications, i.e., enteric coatings.

Batch process and semicontinuous process may be utilized in the practice of this invention; preferably a semicontinuous process is used. In the semicontinuous process, the composition of the feed and the initial charge in the reactor can be varied. The preferred method of feeding program involves feeding monomers/emulsifier/water pre-emulsion into a reactor containing a small portion of monomers and emulsifiers.

Thus, as a further aspect of the present invention, there is provided a process for preparing an enteric polymer of methacrylic acid and ethyl acrylate comprising forming a pre-emulsion in a first step, said pre-emulsion comprising the following components:

(a) about 0.4 to 1.2 weight percent of sodium docusate;

(b) about 0 to 1.0 weight percent of polysorbate 80;

(c) about 30.0 to 60.0 weight percent of water;

(d) about 10.0 to 20.0 weight percent of ethyl acrylate;

(e) about 10.0 to 20.0 weight percent of methacrylic acid;

(f) about 0 to 1.0 weight percent of isopropyl alcohol and/or cysteine hydrochloride;

(g) about 0 to 0.2 weight percent of monthioglycerol; followed by charging a reaction vessel with the following:

(h) about 0.05 to 0.3 weight percent of sodium docusate;

(i) about 0.0 to 0.2 weight percent of polysorbate 80;

(j) about 20.0 to 30.0 weight percent of distilled or deionized water;

(k) about 0.1 to 10.0 weight percent of ethyl acrylate;

(l) about 0.1 to 10.0 weight percent of methacrylic acid; and (m) about 0.02 to 0.15 weight percent of an initiator selected from the group consisting of sodium persulfate, potassium persulfate, ammonium persulfate, hydrogen peroxide, lauryl peroxide, benzoyl peroxide and optionally a compound selected from the group consisting of sodium bisulfite, sodium metabisulfite, sodium dithionate, sodium formaldehyde sulfoxylate, ascorbic acid and salts of $Fe^{+2}$;

followed by feeding the pre-emulsion or co-feeding with portions of initiator solutions into said reaction vessel and heating said reaction vessel to a temperature of about 30° C. to 85° C.; followed by transferring said pre-emulsion to said reaction vessel, and continuing heating until the process is substantially complete.

As noted above, the acrylic polymers of the present invention are useful in coating compositions for medicaments in tablet form. Accordingly, as a further embodiment of the present invention, there is provided a medicament coated with the acrylic polymer of the present invention.

The following examples will further illustrate the invention.

EXPERIMENTAL SECTION

Example 1

A semi-continuous emulsion polymerization was used to make the methacrylic acid-ethyl acrylate enteric polymer. Into a beaker were placed 23.0 g of COMPLEMIX ® 100 (docusate sodium USP), 2.2 g of TWEEN ® 80 (polysorbate 80 NF), 805.0 g of distilled water, 742.0 g of ethyl acrylate, and 685.0 g of methacrylic acid to make the pre-emulsion.

Figure 2:
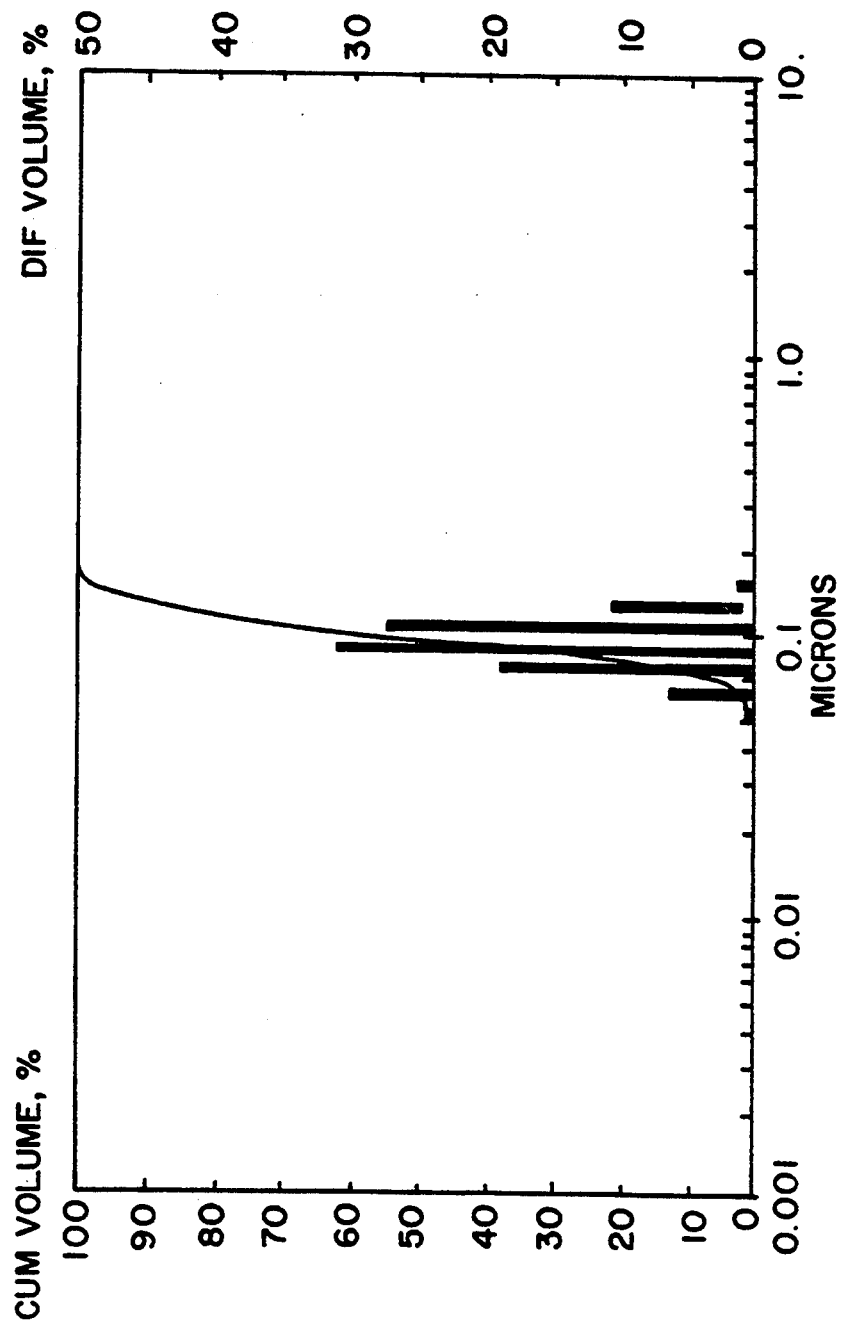
FIG. 2 depicts the particle size distribution of the acrylic enteric polymer of Example 1, below.

Into a 5-liter, 3-neck reactor are placed 10.1 g of COMPLEMIX ® 100, 1.0 g of TWEEN ® 80, 2362.0 g of distilled water, 17.3 g of ethyl acrylate and 15.9 g of methacrylic acid. The reaction mixture is stirred and purged with nitrogen for 30 minutes, while raising the temperatures to 75° C. A total of 125.0 g of 4% potassium persulfate and 45.0 g. of 1% iron II sulfate heptahydrate solutions were charged into the reactor to initiate the copolymerization, followed by feeding the pre-emulsion into the reactor over a 150 minute period. The reaction temperature was maintained at 74°-80° C. for four hours. The emulsion was then cooled to 30° C. Weight average molecular weight is 250,000, and polydispersity is 3.8. Total residual monomer concentration is less than 20 ppm. Particle size distribution is shown in FIG. 2, mean particle size is 0.099 micron, and standard deviation 0.020.

Example 2

The following example demonstrates the use of isopropyl alcohol USP to regulate molecular weight.

Into a beaker were placed 22.5 g of COMPLEMIX 100 (docusate sodium USP), 2.3 of TWEEN 80 (polysorbate 80 NF), 805.0 g of distilled water, 742.0 g of ethyl acrylate, 685 g of methacrylic acid, and 22.0 g of isopropyl alcohol USP to make the pre-emulsion.

Into a 5-liter, three neck reactor were placed 10.0 g of COMPLEMIX 100, 1.0 g of TWEEN 80, 1862.0 g of distilled water, 17.3 g of ethyl acrylate and 15.9 g of methacrylic acid. The reaction mixture was stirred and purged with nitrogen for 30 minutes, while raising the temperature to 75 C. To initiate the copolymerization, 50 g of 4% potassium persulfate and 25 g of 1% iron II sulfate solutions were added to the reactor, followed by co-feeding the pre-emulsion and 575 g of 0.5% potassium persulfate into the reactor over a 155 minute period. The reaction was then maintained at 80 C for four hours; the emulsion was cooled to 30 C, and 145 g of 30% TWEEN 80 was mixed into the emulsion. Weight average molecular weight was determined to be 210,000 and the polydispersity was 5.8. The total residual monomer concentration was less than 20 ppm. Mean particle size was less than 0.110 micron and the standard deviation was 0.026.

Example 3

The following example demonstrates the use of monothioglycerol NF to regulate molecular weight.

The procedure used in this example was substantially the same as that used in example 2, except that 2.6 g of monothioglycerol NF was used in place of 22.0 g of isopropyl alcohol in making the pre-emulsion.

The weight average molecular weight of this example was 205,000 and the polydispersity was 6.5. The total residual monomer concentration was less than 20 ppm. Mean particle size was 116 nm and the standard deviation was 0.026.

Example 4

This example illustrates the use of the methacrylic acid-ethyl acrylate enteric polymers prepared, as described in Example 1, 2, and 3, for coating solid dosage forms.

1. Preparation of coating dope: In a 2-gallon container 338.0 g of USP grade talc is dispersed into 2092.0 g of distilled water. Mix 4670.0 g of the acrylic latex prepared in Example 1, 3, and 3, 1358.0 g of 10% polyethylene glycol aqueous solution, and 15.6 g of a food grade ANTIFORM 1520 from Dow Corning into the solution using a magnetic stirrer. After 30 minutes of mixing, the coating dope is ready for application to solid dosage forms.
2. The coating dope is employed for coating of aspirin tablets (10.5 mm in diameter, 400 mg per tablet (no undercoat)). The coating is performed by spraying the dope on tablets in a Accela-Cota, 24" pilot production coater. Coating conditions are listed in table-1. During coating process, coated tablets are sampled at 8%, 10%, 12%, and 14% by weight of coating per tablet.

TABLE

| Coating Conditions | |
|---|---|
| Parameters | Operating Conditions |
| Batch Size | 10 kg |
| Pan Revolution | 14 rpm |
| Preheating and Dusting Time | 4–8 min |
| Drying Air Temperature | 80° C.–85° C. |
| Spraying Solution Feed | 54.0 ml/min |
| Bed Temperature | 30° C.–35° C. |

These coatings were completed without any problem such as blocking of spray gun, tablet stickiness, etc, during the process. Coated tablets were good, glossy, and elegant in appearance.

Example 5

A coating dope was made using commercial product EUDRAGIT ® L30D USP Methacrylic Acid Copolymer-Type C from Rohm Pharma to coat solid dosage forms. The procedures are the same as described in Example 4, except 4670,0 g of EUDRAGIT ® L30D was used to replace the acrylic latex prepared in Example 1.

The coating was completed with some problems such as solid build up and blocking of spray gun.

Example 6

A modified USP enteric-coated tablet disintegration test specified in page 1578 of USP XXII/NFXVII, the United States Pharmacopeial Convention, Inc, Rockville, Md., 1990 is employed using the USP disintegration test apparatus (Pharma Test Type PTZ 3E) to assess the enteric efficiency of the coated aspirin tablets. These tablets are tested for 2 hours in simulated gastric fluid (pH=1.2) containing NaCl and HCl in water at 37° C. The tablets are then examined to see if the tablets disintegrated and the data recorded in Table 2. Those tablets showing no evidence of disintegration, cracking, or softening are then placed in a simulated intestinal buffer (pH=6.8) containing $KH_2PO_4$ and NaOH in water at 37° C. The disintegration time in the simulated intestinal buffer is less than 20 min for both tablets coated with the acrylic latex prepared in Examples 1, 2, and 3, and with the commercial product EUDRAGIT® L30D USP Methacrylic Acid Copolymer-Type C enteric polymer.

TABLE 2

Modified USP XXII disintegration test of tablets coated with the enteric polymer prepared in Examples 1, 2, and 3, and the commercial product EUDRAGIT ® L30D USP Methacrylic Acid Copolymer - Type C enteric polymer in gastric fluid

| | % Coating | | | |
|---|---|---|---|---|
| | 8 | 10 | 12 | 14 |
| EUDAGRIT ® L30D | Fail | Fail | Fail | Pass |
| Example 1 | Fail | Pass | Pass | Pass |
| Example 2 | Fail | Pass | Pass | Pass |
| Example 3 | Fail | Fail | Pass | Pass |

Fail: evidence of disintegration
Pass: no evidence of disintegration

Figure 3:
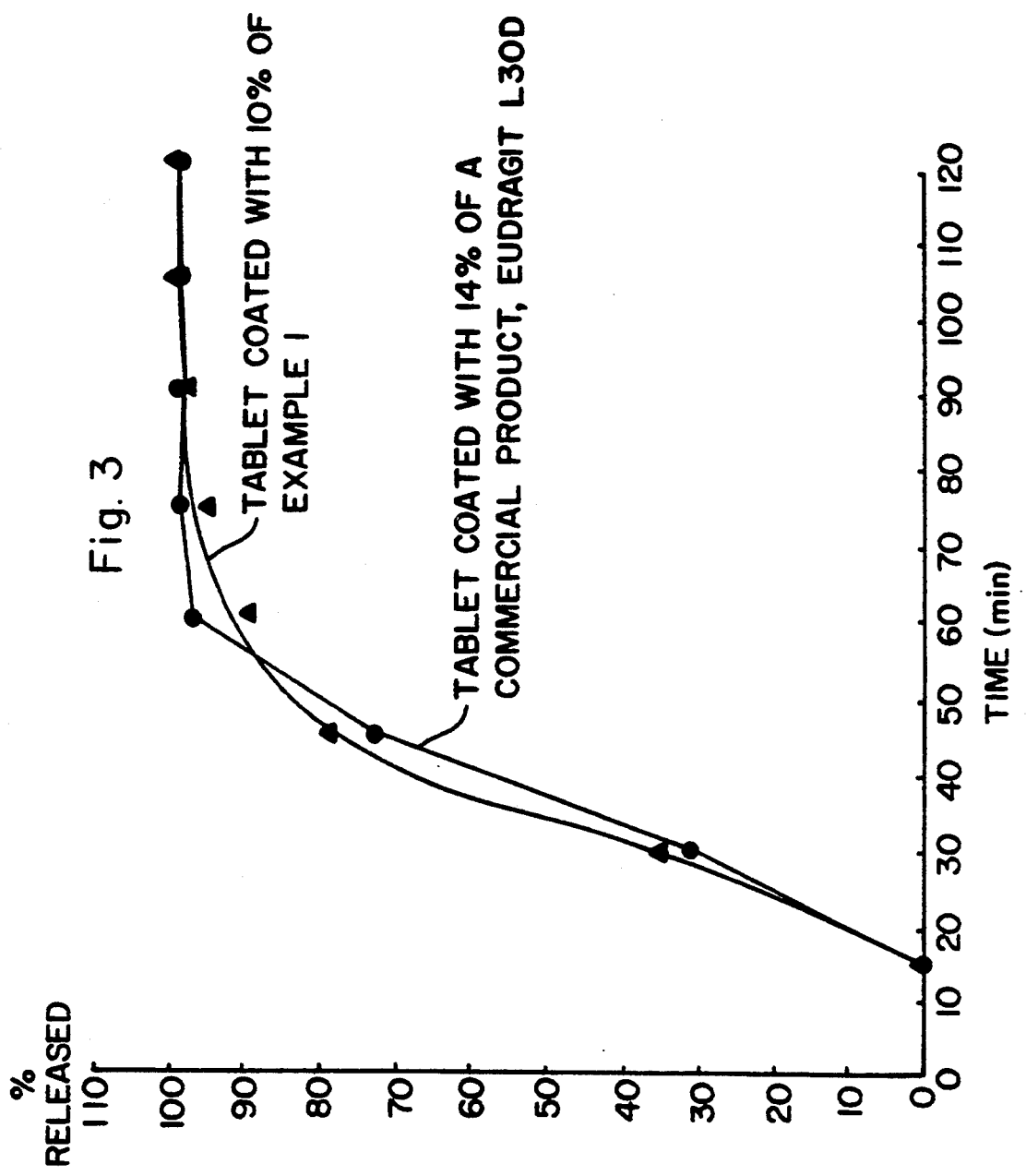
FIG. 3 is a release profile of aspirin tablets coated with 10 weight percent of the enteric polymer of Example 1, below, compared with a 14 weight percent of EUDRAGIT ® L30D acrylic polymer.

Release of aspirin is also evaluated using the USP (basket) Method I at 100 rpm with a Pharma Test Type PTWS. The percent of aspirin released corresponding to the time in a simulated intestinal fluid (pH=6.8) is shown in FIG. 3 for tablets coated with 10% of the enteric polymer prepared in Example 1 of this invention and with 14% of the commercial product EUDRAGIT® L30D USP Methacrylic Acid Copolymer-Type C. The data in Table 2, FIG. 3, and the ease of the tablet coating process, (i.e., no blocking of spray gun) demonstrate the effectiveness of the enteric polymer prepared in this invention. Since the polymer is more effective, less dosage is required to achieve enteric property, cycle time for coating process is reduced, and the reproducibility is improved.

We claim:

1. A process for preparing a polymer of acrylate enteric polymers of methacrylic acid and ethyl acrylate comprising reacting
   (a) about 0.4 to 1.5 weight percent of sodium docusate;
   (b) about 0 to 4.0 weight percent of sorbitan mono-9-octadecenotate poly(oxy-1,2-ethanediyl);
   (c) about 10 to 20 weight percent of ethyl acrylate;
   (d) about 10 to 20 weight percent of methacrylic acid;
   (e) about 0 to 1.0 weight percent of isopropyl alcohol;
   (f) about 0 to 0.2 weight percent monothioglycerol or cysteine hydrochloride;
   (g) about 60 to 75 weight percent of distilled or deionized water; and
   (f) about 0.02 to 0.15 weight percent of an initiator selected from the group consisting of sodium persulfate, potassium persulfate, ammonium persulfate, hydrogen peroxide, lauryl peroxide, benzoyl peroxide and optionally a compound selected from the group consisting of sodium bisulfite, sodium metabisulfite, sodium dithionate, sodium formaldehyde sulfoxylate, ascorbic acid and salts of $Fe^{+2}$; at a temperature of about 30° C. to 85° C.

2. The process of claim 1, wherein component (a) is present in a concentration of about 0.6 to 1.5%.

3. The process of claim 1, wherein component (b) is present in a concentration of about 0.2 to 1.5%.

4. The process of claim 1, wherein the isopropyl alcohol is present in a concentration of about 0.1 to about 0.8%.

5. The process of claim 1, wherein the monothioglycerol or cysteine hydrochloride is present in a concentration of about 0.03 to about 0.15%.

6. A process for preparing an enteric polymer of methacrylic acid and ethyl acrylate comprising forming a pre-emulsion in a first step, said pre-emulsion comprising the following components:
   (a) about 0.4 to 1.2 weight percent of sodium docusate;
   (b) about 0 to 1.0 weight percent of sorbitan mono-9-octadecenoate poly(oxy-1,2-ethanediyl);
   (c) about 30.0 to 60.0 weight percent of distilled or deionized water;
   (d) about 10.0 to 20.0 weight percent of ethyl acrylate;
   (e) about 10.0 to 20.0 weight percent of methacrylic acid;
   (f) about 0 to 1.0 weight percent of isopropyl alcohol; and
   (g) about 0 to 0.2 weight percent of monothioglycerol or cysteine hydrochloride; followed by
charging a reaction vessel with the following:
   (h) about 0.05 to 0.3 weight percent of sodium docusate;
   (i) about 0.0 to 0.2 weight percent of sorbitan mono-9-octadecenoate poly(oxy-1,2-ethanediyl);
   (j) about 20.0 to 30.0 weight percent of distilled or deionized water;
   (k) about 0.1 to 10.0 weight percent of ethyl acrylate;
   (l) about 0.1 to 10.0 weight percent of methacrylic acid; and
   (m) about 0.02 to 0.15 weight percent of an initiator selected from the group consisting of sodium persulfate, potassium persulfate, ammonium persulfate, hydrogen peroxide, lauryl peroxide, benzoyl peroxide and optionally a compound selected from the group consisting of sodium bisulfite, sodium metabisulfite, sodium dithionate, sodium formaldehyde sulfoxylate, ascorbic acid and salts of $Fe^{+2}$; followed by feeding the pre-emulsion or co-feeding with a portion of the initiator solutions into said reacting vessel and heating such reaction vessel to a temperature of about 30° C. to 85° C.; followed by transferring said pre-emulsion to said reaction vessel, and continuing heating until the process is complete.

7. The process of claim 6, wherein component (m) is potassium persulfate or ammonium persulfate.

* * * * *